United States Patent
Parce et al.

[11] Patent Number: 6,149,870
[45] Date of Patent: *Nov. 21, 2000

[54] APPARATUS FOR IN SITU CONCENTRATION AND/OR DILUTION OF MATERIALS IN MICROFLUIDIC SYSTEMS

[75] Inventors: John Wallace Parce, Palo Alto; Anne R. Kopf-Sill, Portola Valley, both of Calif.

[73] Assignee: Caliper Technologies Corp., Mountain View, Calif.

[*] Notice: This patent is subject to a terminal disclaimer.

[21] Appl. No.: 09/407,756

[22] Filed: Sep. 28, 1999

Related U.S. Application Data

[63] Continuation of application No. 09/179,336, Oct. 27, 1998, Pat. No. 6,004,515, which is a continuation of application No. 08/871,338, Jun. 9, 1997, Pat. No. 5,869,004.

[51] Int. Cl.[7] .................... B01L 3/00; B01L 11/00
[52] U.S. Cl. .................. 422/100; 422/68.1; 436/52; 436/179; 436/180; 73/863; 204/600
[58] Field of Search ............... 422/81, 100, 101, 422/63, 68.1, 82, 82.01, 58; 436/52, 174, 179, 180; 73/863; 204/603, 604

[56] References Cited

U.S. PATENT DOCUMENTS

| | | |
|---|---|---|
| 4,036,062 | 7/1977 | Cruzan . |
| 4,070,913 | 1/1978 | Roof . |
| 4,908,112 | 3/1990 | Pace . |
| 4,963,498 | 10/1990 | Hillman et al. . |
| 5,126,022 | 6/1992 | Soane et al. . |
| 5,140,161 | 8/1992 | Hillman et al. . |
| 5,188,963 | 2/1993 | Stapleton . |
| 5,304,487 | 4/1994 | Wilding et al. . |
| 5,391,274 | 2/1995 | Shieh . |
| 5,486,335 | 1/1996 | Wilding et al. . |
| 5,571,410 | 11/1996 | Swedberg et al. . |
| 5,585,069 | 12/1996 | Zanzucchi et al. . |
| 5,593,838 | 1/1997 | Zanzucchi et al. . |
| 5,603,351 | 2/1997 | Cherukuri et al. . |
| 5,605,662 | 2/1997 | Heller et al. . |
| 5,660,703 | 8/1997 | Dasgupta . |
| 5,750,015 | 5/1998 | Soane et al. . |
| 5,869,004 | 2/1999 | Parce et al. ............ 422/100 |
| 6,004,515 | 12/1999 | Parce et al. ............ 422/100 |

FOREIGN PATENT DOCUMENTS

| | | |
|---|---|---|
| WO 9405414 | 3/1994 | WIPO . |
| WO 9604547 | 2/1996 | WIPO . |
| WO 9702357 | 1/1997 | WIPO . |

OTHER PUBLICATIONS

Bao, J. et al., "Ultramicro enzyme assays in capillary electrophoretic system," *J. Chrom.* 608:217–224 (1992).

Dasgupta, P.K. et al., "Electroosmosis: A Reliable Fluid Propulsion System for Flow Injection Analysis," *Anal. Chem.* 66:1792–1798 (1994).

(List continued on next page.)

*Primary Examiner*—Lyle A. Alexander
*Attorney, Agent, or Firm*—Mathew B. Murphy; Gulshan H. Shaver

[57] ABSTRACT

The present invention is generally directed to methods, apparatus and systems for use in performing in situ dilution or concentration of a particular subject material in a microfluidic device or system. These methods and apparatus may generally be integrated with other microfluidic operations and/or systems, to perform a number of different manipulations, wherein dilution or concentration, carried out within the context of the microfluidic device or system, is just one part.

22 Claims, 5 Drawing Sheets

OTHER PUBLICATIONS

Harrison, D.J. et al., "Micromachining a Miniaturized Capillary Electrophoresis–Based Chemical Analysis System on a Chip," *Science* 261:895–897 (1993).

Jacobson, S.C. et al., "Precolumn Reactions with Electrophoretic Analysis Integrated on a Microchip," *Anal. Chem.* 66:4127–4132 (1994).

Jacobson, S.C. et al., "Fused Quartz Substrates for Microchip Electrophoresis," *Anal. Chem.* 67:2059–2063 (1995).

Linhares, M.C. et al., "Use of an On–Column Fracture in Capillary Zone Electrophoresis for Sample Introduction," *Anal. Chem.* 63:2076–2078 (1991).

Manz, A. et al., "Miniaturized Total Chemical Analysis Systems: a Novel Concept for Chemical Sensing," *Sensors and Actuators* B1:244–248 (1990).

Manz, A. et al., "Micromachining of monocrystalline silicon and glass for chemical analysis systems," *Trends in Anal. Chem.* 10(5):144–149 (1991).

Manz, A. et al., "Electroosmotic pumping and electrophoretic separations for miniaturized chemical analysis systems," *J. Micromech. Microeng.* 4:257–265 (1994).

Ramsey, J.M. et al., "Microfabricated and chemical measurement systems," *Nature Med.* 1:1093–1096 (1995).

Seiler, K. et al., "Planar Glass Chips for Capillary Electrophoresis: Repetitive Sample Injection, Quantitation, and Separation Efficiency," *Anal. Chem.* 65:1481–1488 (1993).

Seiler, K. et al., "Electroosmotic Pumping and Valveless Control of Fluid Flow Within a Manifold of Capillaries on a Glass Chip," *Anal. Chem.* 66:3485–3491 (1994).

Woolley, A.T. et al., "Ultra–high–speed DNA fragment separations using microfabricated capillary array electrophoresis chips," *Proc. Natl. Acad. Sci. U.S.A.* 91:11348–11352 (1994).

APPARATUS FOR IN SITU CONCENTRATION AND/OR DILUTION OF MATERIALS IN MICROFLUIDIC SYSTEMS

CROSS REFERENCE TO RELATED APPLICATION

This application is a continuation of U.S. patent application Ser. No. 09/179,336, filed Oct. 27, 1998, now U.S. Pat. No. 6,004,515, which is a continuation of U.S. patent application Ser. No. 08/871,338, filed Jun. 9, 1997, now U.S. Pat. No. 5,869,004.

BACKGROUND OF THE INVENTION

Carrying out chemical or biochemical analyses, syntheses or preparations, even at the simplest levels, requires one to perform a large number of separate manipulations on the material components of that analysis, synthesis or preparation, including measuring, aliquoting, transferring, diluting, concentrating, separating, detecting etc.

In developing microfluidic technologies, researchers have sought to miniaturize many of these manipulations and/or to integrate these manipulations within one or a few microscale devices. Many of the above described manipulations easily lend themselves to such miniaturization and integration. For example, the use of these microfluidic technologies has been described in a number of applications, including, e.g., amplification (U.S. Pat. Nos. 5,587,128 and 5,498,392) and separation of nucleic acids (Woolley et al., Proc. Nat'l. Acad. Sci. 91:11348-352 (1994) and hybridization analyses (WO 97/02357 to Anderson).

Despite the application of microfluidic technologies to these manipulations, there are still a number of areas where that application is not so easily made. For example, the performance of large dilutions generally requires the combination of a small volume of the material that is desired to be diluted with a large volume of diluent. By definition, microfluidic systems have extremely small overall volumes, and are typically unable, or less able, to handle the larger volumes required for such dilutions. Further, such large dilutions also typically require the accurate, repeatable dispensing of extremely small volumes of the material to be diluted. However, most microfluidic technology is incapable of accurately dispensing fluid volumes substantially less than a microliter. Although the problems associated with the inability to aliquot extremely small volumes might generally be overcome by performing serial dilutions, such serial dilutions generally require devices with substantially larger volumes, e.g., tens or hundreds of microliters. Specifically, even if one assumes a lower limit of fluid handling of 100 nanoliters, a 1:10 dilution would require a device to handle at least a volume of 1 $\mu$l. Further serial dilution steps only increase the required volume.

It would therefor be desirable to provide microfluidic systems which are capable of performing each of the various manipulations required, and which are capable of doing so with a sufficiently small volume whereby, multiple operations can be integrated into a single low volume device or system and performed automatically and with a high degree of precision. Of particular interest would be a microfluidic device or system, as well as methods for using such devices and systems for performing in situ dilution or concentration of a particular material within a microfluidic format. The present invention meets these and many other needs.

SUMMARY OF THE INVENTION

The present invention is generally directed to methods, apparatus and systems for performing in situ concentration or dilution of a material in microfluidic devices or systems. In one aspect, the present invention provides microfluidic devices and systems for performing in situ dilution, and particularly in situ serial dilution, of a particular subject material. The devices and/or systems typically comprise a microfluidic device which has at least one main channel disposed therein, where the main channel has at least one microscale cross-sectional dimension. The devices and/or systems also typically comprise at least a first source of the subject material that is to be diluted, in fluid communication with the main channel at a first point along the length of the channel, at least a first source of diluent in fluid communication with the main channel at a second point along the length of the channel, and at least a first reservoir in fluid communication with the main channel at a third point along the length of the channel. The systems of the present invention further comprise a fluid direction for delivering diluent to the main channel to be combined with the subject material to form first diluted material, and for removing at least a portion of the first diluted material from the main channel to the reservoir. Additional diluent sources and reservoirs also may be supplied to further dilute the subject material.

In a closely related aspect, the present invention provides a microfluidic system for continuously diluting a subject material within a microfluidic device. The devices and/or systems typically comprise a microfluidic device which has at least one main channel disposed therein, where the main channel has at least one microscale cross-sectional dimension. The device also typically comprises at least a first source of the subject material in fluid communication with the main channel at a first point along the length of the channel, at least a first source of diluent in fluid communication with the main channel at a second point along the length of the channel, and at least a first reservoir in fluid communication with the main channel at a third point along the length of the channel. The systems of the present invention further comprise a fluid direction system for continuously delivering diluent to the main channel to be combined with the subject material to form first diluted material, and continuously transporting a portion of the first diluted material from the main channel to the reservoir.

The present invention also provides microfluidic systems for in situ concentration of a subject material within a microfluidic device. In this aspect, the system comprises a microfluidic device having a first channel disposed therein, which channel has first, second and third fluid regions disposed therein. The first fluid region typically comprises the subject material and has a first conductivity, whereas the second and third fluid regions are disposed within the first channel on both ends of the first fluid region. The second and third fluid regions have a second conductivity, where the second conductivity is greater than the first conductivity. The system also typically comprises an electroosmotic fluid direction system for transporting the first and second fluid regions along the first channel.

In a further aspect, the present invention provides methods for in situ dilution of a subject material in a microfluidic device. The methods typically comprise combining a first volume of the subject material with a first volume of diluent in a first microscale channel to form a first diluted material. At least a first portion of the first diluted material is then transported out of the first channel. A second volume of diluent from a second diluent source is then delivered to the first microscale channel to combine the second volume of diluent with a second portion of the first diluted material to form a second diluted material.

In a related aspect, the present invention provides a method for in situ dilution of a material in a microfluidic device, which method comprises combining a first volume of said material with a first volume of diluent in a first region of a microfluidic device to form a first diluted material. A portion of the first diluted material is then transported into a second region of the microfluidic device, i.e., a reservoir, where it is combined with a second volume of diluent to form a second diluted material.

In a further aspect, the present invention provides a method for the in situ concentration of a material in a microscale channel. The method comprises introducing a first fluid containing the material into a microscale channel to provide a first fluid region within the channel. The first fluid has a first conductivity, and is bounded by second and third fluid regions, where the second and third fluid regions have a second conductivity which is greater than the first. A voltage gradient is then applied along the length of the microscale channel whereby the first, second and third fluid regions are transported along the length of the microscale channel with a first electroosmotic mobility, and whereby the material in the first fluid has an electrophoretic mobility different from the electroosmotic mobility, resulting in a concentration of the subject material at or near one end of the first fluid region.

BRIEF DESCRIPTION OF THE FIGURES

FIG. 5A illustrates the structure of the element, whereas FIGS. 5B through 5E illustrate the operation of the concentrator element in concentrating a particular subject material.

DETAILED DESCRIPTION OF THE INVENTION

I. Generally

Figure 1:
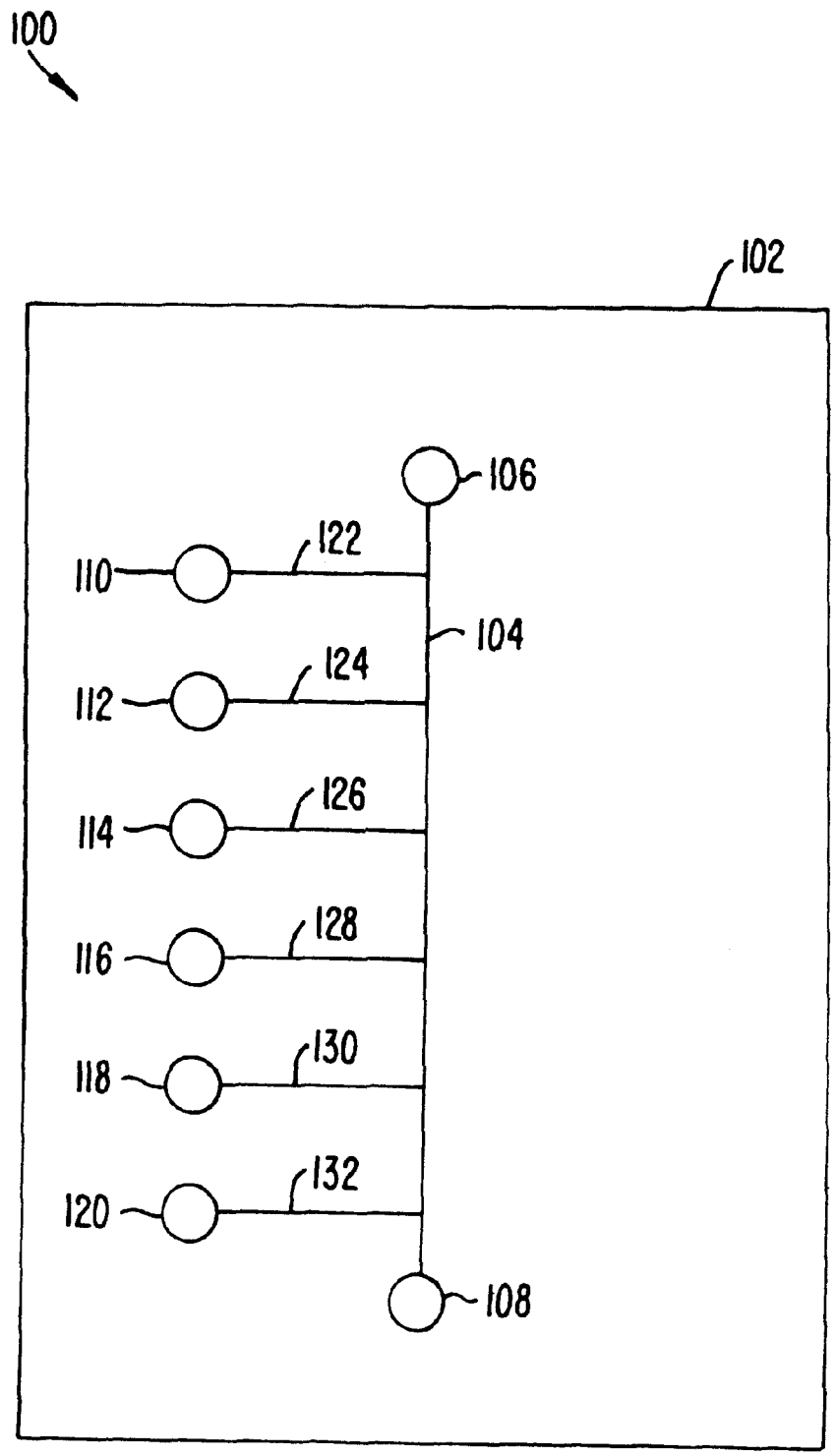
FIG. 1 is a schematic illustration of an embodiment of a microfluidic device for performing continuous serial dilution of a subject material.

The present invention is generally directed to methods, apparatus and systems for use in performing in situ dilution or concentration of a particular subject material in a microfluidic device or system. These methods and apparatus may generally be integrated with other microfluidic operations and/or systems, to perform a number of different manipulations, wherein dilution or concentration, carried out within the context of the microfluidic device or system, is just one part of the overall operation.

The term "dilution," as used herein, generally encompasses the ordinary meaning of that term, namely, the reduction in the amount of a particular subject material per unit volume of a fluid containing that material, through the addition of a second fluid, or diluent, to a first fluid which contains the subject material, e.g., soluble chemical component, or a suspension or emulsion of a partially insoluble material, whereby the resulting concentration of the subject material is reduced over that of the first fluid. In terms of the present invention, the diluent may take on a variety of forms, including aqueous or nonaqueous fluids and/or it may include additional material components, e.g., soluble chemical components or suspensions or emulsions of at least partially insoluble components. As alluded to above, the subject material may comprise virtually any composition, including chemical compounds, either soluble or as suspensions or emulsions, biological material, either soluble or as suspensions (e.g., cells) or emulsions, and the like. By "serial dilution" is generally meant successive dilutions, as defined herein, wherein the subject material is diluted with diluent to form a first diluted material, which first diluted material is then diluted with a diluent again, to produce a second diluted material, etc. For example, one produces a first diluted material that is diluted 1:10 over the subject material. By then diluting at least a portion of this material 1:10, one produces a second diluted material that is a 1:100 dilution of the subject material. In general, the methods, devices and systems of the present invention are useful in diluting subject material greater than 10 fold (1:10), typically greater than 100 fold (1:100), preferably greater than 1000 fold (1:1000), and in many cases, greater than 10,000 fold (1:10,000), within a single integrated microfluidic device, which typically has an internal volume, e.g., channel volume, of less than 10 µl and preferably less than 1 µl.

The term "concentration" as used herein, generally refers to the ordinary meaning of that term, namely the increase in the amount of a particular subject material per unit volume of the fluid in which the material is disposed, e.g., wholly or partially dissolved, suspended, slurried, etc.

As used herein, the term "microfluidic," or the term "microscale" when used to describe a fluidic element, such as a passage, chamber or conduit, generally refers to one or more fluid passages, chambers or conduits which have at least one internal cross-sectional dimension, e.g., depth or width, of between about 0.1 µm and 500 µm. In the devices of the present invention, the microscale channels preferably have at least one cross-sectional dimension between about 0.1 µm and 200 µm, more preferably between about 0.1 µm and 100 µm, and often between about 0.1 µm and 20 µm. Accordingly, the microfluidic devices or systems of the present invention typically include at least one microscale channel, and preferably at least two intersecting microscale channels disposed within a single body structure.

The body structure may comprise a single component, or an aggregation of separate parts, e.g., capillaries, joints, chambers, layers, etc., which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device. In preferred aspects, the bottom portion will comprise a solid substrate that is substantially planar in structure, and which has at least one substantially flat upper surface. A variety of substrate materials may be employed as the bottom portion. Typically, because the devices are microfabricated, substrate materials will generally be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, particularly where electric fields are to be applied.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such substrates are readily manufactured from microfabricated masters, using well known molding techniques, such as injection molding, embossing or stamping, or by polymerizing the polymeric precursor material within or against the mold or master. Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. Pat. No. 5,885,470, and which is incorporated herein by reference in its entirety for all purposes.

The channels and/or chambers of the microfluidic devices are typically fabricated into the upper surface of the substrate, or bottom portion, using the above described microfabrication techniques, as microscale grooves or indentations. The lower surface of the top portion of the microfluidic device, which top portion typically comprises a second planar substrate, is then overlaid upon and bonded to the surface of the bottom substrate, sealing the channels and/or chambers (the interior portion) of the device at the interface of these two components. Bonding of the top portion to the bottom portion may be carried out using a variety of known methods, depending upon the nature of the substrate material. For example, in the case of glass substrates, thermal bonding techniques may be used which employ elevated temperatures and pressure to bond the top portion of the device to the bottom portion. Polymeric substrates may be bonded using similar techniques, except that the temperatures used are generally lower to prevent excessive melting of the substrate material. Alternative methods may also be used to bond polymeric parts of the device together, including acoustic welding techniques, or the use of adhesives, e.g., UV curable adhesives, and the like.

The microfluidic devices and systems of the present invention, e.g., which are capable of performing in situ dilution or concentration of a particular subject material, typically comprise a main microscale channel disposed within the body structure, which is used to transport, and in some embodiments, mix the subject material and the diluent. Accordingly, the devices of the present invention comprise at least a first source of fluid containing a particular subject material in fluid communication with the main channel. For those aspects of the present invention directed to dilution of the subject material, a source of diluent is also generally provided in fluid communication with the main channel. Typically, the source of material and the source of diluent are provided as an integral part of the body structure, e.g., as wells or reservoirs within the body structure, e.g., the top portion of the device. Fluid communication between these sources and the main channel is generally via a connecting channel which is in fluid communication with the well or reservoir at one end, and in fluid communication with, e.g., intersecting, the main channel at the other end.

In order to manipulate materials within the microfluidic devices described herein, the overall microfluidic systems of the present invention typically include a material direction system to manipulate selected materials within the various channels and/or chambers of the microfluidic device. Thus, by "material direction system" is meant a system which controls the movement and direction of fluids containing such materials within intersecting channel structures of a microfluidic device. Generally, such material direction systems employ pumps or pressure systems, and valves to affect fluid movement and direction in intersecting channels. A large number of microfabricated mechanical pumps and valves have been previously described in the art. Although such fluid direction elements may be useful in many aspects of the present invention, by and large, these elements are not preferred due to the complexity and cost of their manufacture. Further, the limits of microfabrication technology with respect to such pumps and valves, do not readily permit the manufacture of such elements that are capable of precisely handling sufficiently small volumes, e.g., volumes less than 1 $\mu$A. Thus, in particularly preferred aspects, the microfluidic systems of the present invention employ electroosmotic material direction systems to affect direction and transport of fluid borne materials within the microfluidic devices and systems of the invention. "Electroosmotic material direction systems," as used herein, refer to material direction systems which employ controlled electroosmotic flow to affect fluid movement and direction in intersecting channel structures. In particular, such systems function by applying a voltage gradient across the length of a fluid filled channel, the surface or walls of which have charged or ionizeable functional groups associated therewith, to produce electroosmotic flow of that fluid within that channel. Further, by concurrently regulating flow in two or more channels that meet at an intersection, one can direct fluid flow at that intersection. Such electroosmotic material direction systems and controllers are described in detail in, e.g., Published PCT Application No. 96/04547 to Ramsey et al., U.S. application Ser. No. 08/691,632, filed Aug. 2, 1996 and U.S. Pat. No. 5,779,868, each of which is incorporated herein by reference in its entirety for all purposes.

II. Dilution

As described above, in a first aspect, the present invention generally provides methods, devices and systems for performing the in situ dilution, and particularly serial dilution, of a subject material within a microfluidic device or system.

Dilution of the subject material in microfluidic devices and systems according to the present invention, generally comprises transporting a first volume of fluid containing the subject material from the reservoir containing that subject material, into the main channel, and mixing that first volume with a second volume of diluent transported into the main channel from the reservoir of diluent, to produce a first diluted material. The first diluted material is then further diluted by combining a portion of the first diluted material with another volume of diluent to produce a second diluted material. These dilution steps may be repeated any number of times until the desired dilution is achieved.

In preferred aspects, the process of mixing the fluid containing the subject material and the diluent preferably is carried out within the main channel. In particular, the first volume of the fluid containing the subject material is delivered from the source of the subject material into the main channel, while a second volume of diluent is transported from the diluent source into the main channel. The mixing of these two fluids within the main channel produces the first diluted material. This first diluted material is then combined with a further volume of diluent to produce a second diluted material, and so on.

However, because volumes of microfluidic devices and/or systems are extremely small and therefore limited, in order to further dilute the first diluted material, e.g., in a serial dilution, one must transport at least a portion of the first diluted material out of the main channel, e.g., out of the device or into a waste reservoir, prior to delivering the further volume of diluent, in order to accommodate that additional volume of diluent. Once the first diluted material is transported out of the main channel, a further volume of diluent is delivered to the main channel and combined with the remaining portion of the first diluted material, which, upon mixing, produces a second diluted material which is the product of the first and second dilutions, e.g., if the first and second dilutions were each 10 fold, then the second diluted material would be a 100 fold dilution of the starting material.

One example of a microfluidic device for carrying out in situ serial dilution as described herein, is schematically illustrated in FIG. 1. As shown, the device 100, includes a body structure 102 which has a main channel 104 disposed therein. As shown, a source of, or reservoir containing the subject material 106 is provided in fluid communication with the main channel. The illustrated device also includes multiple diluent sources 110, 114 and 118 in fluid communication with the main channel via diluent channels 122, 126 and 130, respectively. The device also includes reservoirs 112, 116 and 120 in fluid communication with the main channel via reservoir channels 124, 128 and 132, respectively. The main channel is also shown with a terminal waste reservoir 108 at its terminus. Although illustrated in terms of performing only dilutions of the subject material, it will be appreciated from the instant disclosure that this device or aspect of a device is readily integrated into a device or system which performs numerous other manipulations, including enzyme assays, immunoassays, screening assays, separations and the like. As a result, waste reservoir 108 may generally be substituted with appropriate fluidic elements for performing further manipulations of the ultimately diluted material, e.g., analysis, reaction, detection, etc.

In operation, a first volume of the subject material from reservoir 106 is flowed into the main channel 104. This volume of subject material is combined with a first volume of diluent which is flowed into main channel 104 from diluent reservoir 110, via channel 122. While flowing down the main channel towards reservoir 108, the subject material and the diluent will mix to form a first diluted material. A portion of this first material is then directed from the first channel into reservoir channel 124 and out to reservoir 112, while the remaining portion of first diluted material continues to flow down the length of the main channel towards reservoir 108. This remaining portion of first diluted material is then combined with a second volume of diluent delivered into main channel 104 from diluent reservoir 114 via channel 126, whereupon, the second volume of diluent and first diluted material will mix to form a second diluted material flowing down the main channel towards reservoir 108. For ease of discussion, each step of directing a portion of the diluted material out of the main channel and delivering a volume of diluent into the channel to combine with the remaining portion of diluted material is referred to herein as a dilution stage. A portion of this second diluted material is then directed from the first channel into reservoir channel 128 and out to reservoir 116, while the remaining portion of second diluted material continues to flow down the main channel towards reservoir 108. The remaining portion of the second diluted material is then combined with a third volume of diluent delivered into main channel 104 from diluent reservoir 118 via channel 130, whereupon the third volume of diluent and the remaining portion of the second diluted material will mix to form a third diluted material. This third diluted material may then be subjected to a subsequent analysis, reaction, combination etc. However, in preferred aspects, and as shown in FIG. 1, a portion of the third diluted material in main channel 104 is transported out of the main channel and into reservoir 120, via channel 132. This allows the stepping down of the volume of third diluted material which must be subsequently handled.

The steps of delivering diluent to the main channel and transporting portions of diluted material out of the main channel may be repeated as necessary in order to produce the dilution ratio desired. In addition, although described in terms of volumes of material and diluent, the devices of the present invention as they relate to dilution, preferably are run in a continuous flow arrangement. Specifically, subject material is flowed into the main channel in a stream at a first flow rate, while a stream of diluent is concurrently flowed into the main channel at a second flow rate, where the ratio of first flow rate to second flow rate are related to the desired dilution for that particular dilution step. These streams mix within the main channel to form a stream of first diluted material. Similarly, a portion of the stream of first diluted material is continuously flowed out of the main channel into the reservoir channel and out to the reservoir, while downstream, another stream of diluent is introduced into the main channel to mix with the remaining portion of the stream of first diluted material to produce second diluted material. These steps are repeated on down the main channel to form a continuous stream of material at the desired dilution as long as flow is maintained into and out of the main channel at the appropriate rates to affect the incremental dilutions at each dilution stage.

The dilution methods and systems described herein are particularly useful in microfluidic systems which employ electroosmotic fluid direction systems. In these electroosmotic fluid direction systems, fluid flow is generally proportional to current flow. Accordingly, in performing dilutions using these systems, the dilution ratio is generally related to the ratio of current applied at the subject material reservoir to the current applied to the diluent reservoir. For relatively small dilutions, e.g., 1:10, these electroosmotic systems can carry out the desired dilution in one step, e.g., combining 1 part subject material to 9 parts diluent, or applying 1 $\mu$A to the subject material reservoir and 9 $\mu$A to the diluent reservoir. However, for dilutions somewhat greater than 1:10, diffusional leakage of the subject material from its supply channel into the main channel limits further dilution, even where only extremely small currents are applied at the subject material reservoir.

One potential solution to the problem of diffusional leakage is to perform multiple serial dilutions, e.g., perform three successive 10 fold dilutions. However, because fluid flow is related to current flow, the final dilution would require a current applied at the dilution well of 900 $\mu$A. Specifically, the first dilution would be carried out by applying 1$\mu$A to the subject material reservoir while applying 9 µA to the diluent reservoir, resulting in a 10 µA current in the main channel. The second 1:10 dilution would then require a current of 90 µA in the second diluent reservoir, and create a current of 100 µA in the main channel. The final dilution would then require an applied current at the third diluent reservoir of 900 µA, which would create a large number of adverse effects on the microfluidic system, electrolysis of the buffers, excessive heating of the fluid channels, etc.

As described above, the methods and systems of the present invention combine the subject material with diluent to create a first diluted material. A portion of this diluted material is then removed from the main channel and the remaining portion is further diluted. This process allows one to perform serial dilutions as described above, the methods and systems of the present invention combine the subject material with diluent microfluidic systems, thereby obviating the problem of diffusional leakage at the intersections, as well as permitting much larger dilutions. Furthermore, this process allows for the use of electroosmotic fluid direction systems without requiring excessive current ratios, and thus, application of excessive currents.

Referring to the system illustrated in FIG. 1, a particular subject material disposed in reservoir 106, is diluted up to 1,000 fold using these methods. In particular, a first 10 fold dilution of the subject material is achieved by applying 1 µA to reservoir 106, while applying 9 µA to the first diluent reservoir 110, resulting in a 9 to 1 ratio of diluent flow to subject material flow. This also results in a 10 µA current within the main channel 104, between its intersection with channel 122 and its intersection with channel 124. A current of −9 µA is applied at waste reservoir 112, which results in approximately 90% of the diluted material flowing to the waste reservoir from the main channel, and returns current in the main channel to 1 µA between its intersection with channel 124 and its intersection with channel 126. Again, a 9 µA current is applied in second diluent reservoir 114, resulting in a further 1:10 dilution of the subject material within the main channel, or a total dilution of 1:100. Another −9 µA current is then applied at waste reservoir 116, withdrawing approximately 90% of the second diluted material, and the final dilution step is supplied by applying 9 µA at third diluent reservoir 118. A further waste reservoir 120 is also shown, for reducing the current at the final waste reservoir 108, back to 1 µA. Accordingly, a 1000 fold dilution only requires a 10 fold current range across the device. Further, because each dilution step is relatively modest, e.g., 1:10, these methods do not suffer from the problems of diffusional leakage at the combining intersection, because the smallest volume is easily controlled at these levels.

Figure 2:
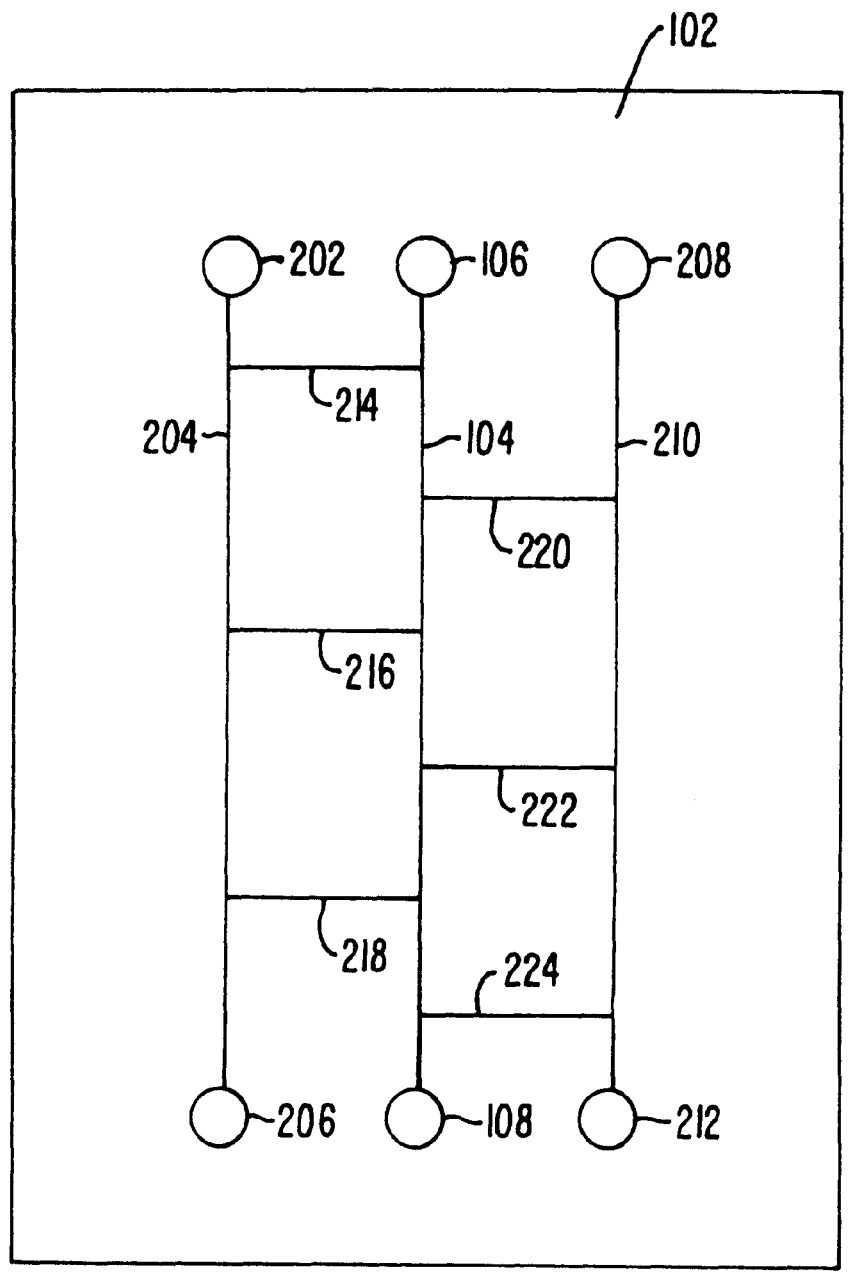
FIG. 2 is a schematic illustration of an alternate embodiment of a microfluidic device for performing continuous serial dilution of a subject material.

An alternative structure that can be used in practicing the dilution methods described herein, is shown in FIG. 2. This alternate structure has the advantage of including a potentially unlimited number of dilution stages while only requiring six reservoirs at which electrical contact is made. As shown, the channel structure is shown fabricated in a substrate 102 and again includes subject material reservoir 106, main channel 104 and waste reservoir 108. In addition, the structure includes a main diluent channel 204 which has at its termini diluent reservoirs 202 and 206, and main waste channel 210 which has at its termini waste reservoirs 208 and 212. Main diluent channel 204 is in fluid communication with main channel 104 via a plurality of diluent connecting channels 214, 216 and 218. Similarly, main waste channel 210 is in fluid communication with main channel 104 via waste connecting channels 220, 222 and 224, which are staggered from the diluent connecting channels, e.g., diluent connecting channel 214 intersects main channel 104 at a first point, and waste connecting channel 220 intersects the main channel 204 at a second point, that is further downstream from the first point.

In operation, subject material from reservoir 106 is introduced into main channel 104, e.g., by applying a current along the length of channel 104. A first volume of diluent is introduced into the main channel from main diluent channel 204, via diluent connecting channel 214, to create a first diluted material, which continues to flow toward reservoir 108. After the subject material and diluent mix, a first portion of the first diluted material is transported out of main channel 104 into main waste channel 210, via waste connecting channel 220. A second volume of diluent is then delivered to the main channel 104 from main diluent channel 204, via diluent connecting channel 216, whereupon it will mix with the remaining portion of first diluted material to form a second diluted material. A portion of this second diluted material is then transported out of channel 104 into the main waste channel 210 via waste connecting channel 222. The process steps are then repeated, e.g., with diluent connecting channel 218 and waste connecting channel 224, as necessary to achieve the desired dilution. As shown, the channel structure includes three dilution stages. However, as noted previously, the structure shown can include additional dilution stages without necessitating additional reservoirs. For example, in the figure shown, application of a first voltage to reservoirs 106, 202 and 208, and a second voltage to reservoirs 108, 206 and 212 will cause material to move in parallel down each of main diluent channel 204, main channel 104, and main waste channel 210, with no dilution of the subject material in main channel 104. Specifically, no material will move among the various main channels. Increasing the potentials at reservoirs 202 and 206, while symmetrically reducing the potentials applied at reservoirs 208 and 212, relative to the potentials applied at reservoirs 106 and 108, will cause dilution to occur in the main channel 104. Specifically, application of these voltage gradients will cause diluent to flow from main diluent channel 204 through diluent connecting channels 214, 216 and 218, diluting the subject material present in the main channel at the intersection of the main channel and each of the diluent connecting channels. Similarly, material in the main channel, in addition to flowing toward reservoir 108, will also be flowing out of main channel 104 via waste connecting channels 220, 222 and 224 and thereby creating room for incoming diluent in a subsequent stage.

In addition to the foregoing, it will be appreciated from the instant disclosure, that the length of the diluent and waste channels in FIGS. 1 and 2 may be adjusted, in order to obviate the need for a wide range of applied voltages to achieve the desired currents. Specifically, higher voltages are required to achieve a certain desired current in a channel with higher resistance. By reducing the length of the channel, one also reduces the resistance along the length of that channel.

As will be apparent from the disclosure of the invention herein, in many of the embodiments described, either the flow rates of the materials and diluents, or the length of the main channel between the diluent channels and the waste channels are selected whereby the subject material and the diluent are permitted to adequately mix before a portion of these materials is transported out of the main channel. These parameters will typically vary depending upon the diffusion rate for the material being transported, the length of the channel along which the material is being transported, and the flow velocity of the material being transported. Generally, however, these parameters are readily determinable with only routine experimentation, and may be readily optimized depending upon the overall system used.

Both structures illustrated in FIGS. 1 and 2, provide for dilution of the subject material based upon the currents or voltages applied to the device, as well as the number of dilution modules or stages fabricated into the device. In a further modified aspect, the present invention also provides a dilution module that yields a given dilution of the subject material regardless of the current applied through the system, effectively "hard-wiring" a particular dilution factor into the device.

Figure 3:
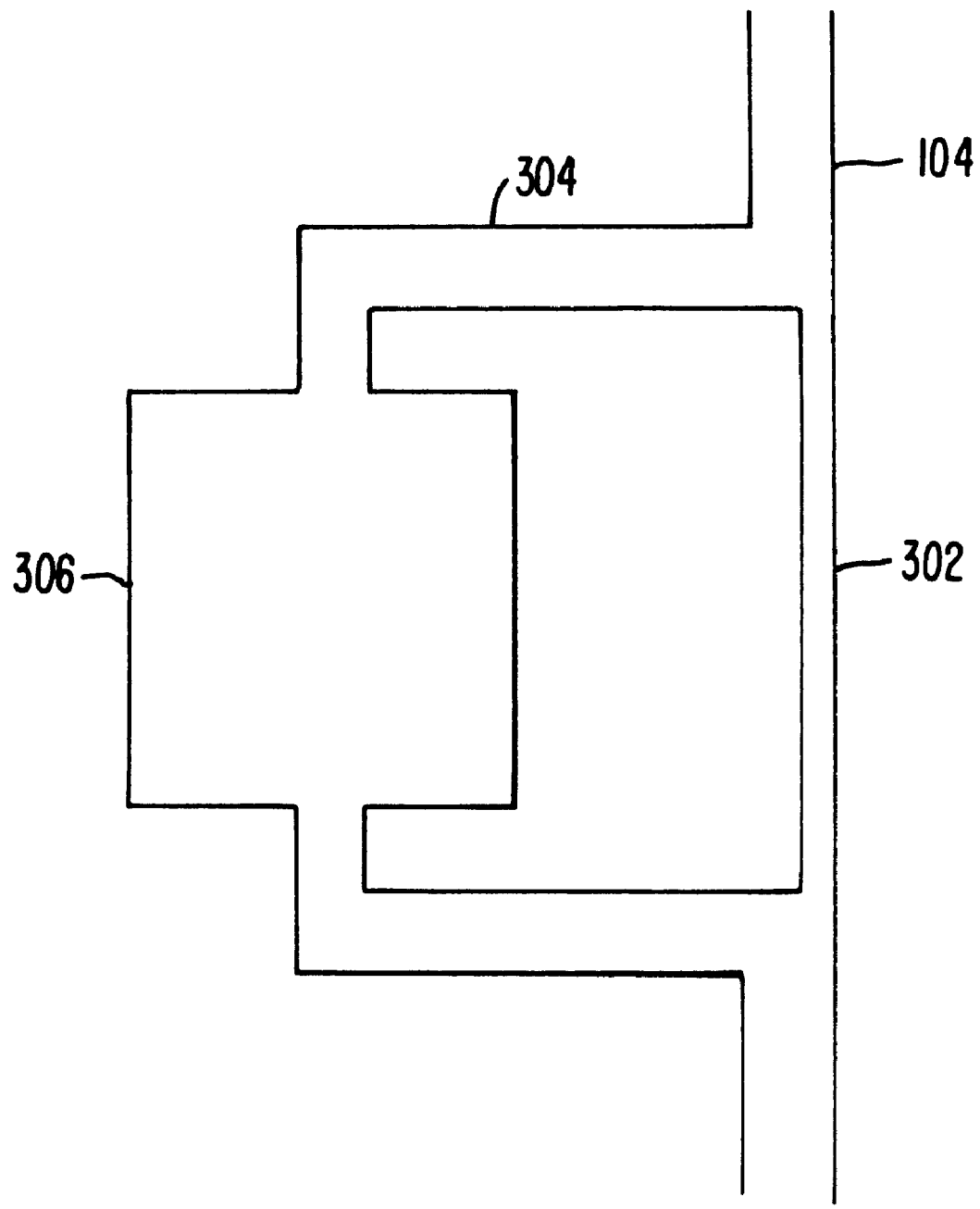
FIG. 3 is a schematic illustration of an embodiment of a passive dilution module incorporated into a microfluidic device according to the present invention.

A schematic illustration of one example of such a dilution module is shown in FIG. 3. As shown in FIG. 3, the device again includes a main channel 104, which includes a narrowed region 302. Bypass channel 304 fluidly connects with main channel 104 above and below narrow region 302, i.e., upstream and downstream of the narrow region, and includes a diluent reservoir 306, disposed therein. In particular, diluent reservoir 306 is an integral part of the bypass channel 304. Reservoir 306 typically has a volume that is sufficiently larger than the volume of the channels, such that regardless of the flow of subject material into the reservoir via bypass channel 304, the effluent from the reservoir has an insignificant concentration of subject material. Because of the extremely small volumes of material required in these microfluidic systems, effective volumes of this diluent reservoir can be on the order of 1 to 10 $\mu$l, and less, depending upon the flow rate used, the length of time the dilution is to run and the like. The increased volume of diluent reservoir 306 may be provided by increasing the length, width and/or depth of the reservoir relative to the channels of the device.

The size of the dilution accomplished by this type of dilution module is dictated by the ratio of the resistance of channel 302 to the resistance of the loop defined by channels 304 and reservoir 306, regardless of the level of current flowing through the dilution module as a whole. In particular, as noted above, in electroosmotic flow systems, fluid flow is proportional to the level of current flow along a channel, which is inversely proportional to the resistance along a given channel. The resistance through a given fluid filled channel is inversely proportional to the cross sectional area, and directly proportional to the length of the channel through which current is passed. Accordingly, by adjusting the resistance along two potential current paths in a fluidic system, one can control the amount of electroosmotic fluid flow along each of the channels. For example, if fluid channels A and B begin and terminate in fluid communication, one can flow approximately 90% of fluid along path A by providing 90% of the current along this path. This is done by increasing the resistance along path B relative to path A. One simple method of increasing this resistance is to narrow the cross sectional dimensions of path B relative to path A. As can be appreciated, other methods may also be used to increase the resistance along path B, including increasing the length of path B relative to path A.

Thus, as can be readily appreciated from the above, and with reference to FIG. 3, the ratio of subject material flowing out of main channel 104, and thus, the amount of diluent flowing into the main channel below the narrow region 302, to the amount of material flowing through the narrow region 302, is proportional to the ratio of the resistance of the narrow region to that of the bypass region. This is the case regardless of the amount of current flowing through the system. Dilution occurs at the lower end of the narrow region, where subject material flowing into reservoir 306 displaces an equal volume of diluent, which flows into the main channel at the lower end of the narrow region and mixes with the portion of subject material that traveled through the narrow region, to create a first diluted material. Because the diluent reservoir 306 has a sufficiently large volume, as compared with the amount of subject material flowing therein, the effluent is substantially entirely diluent. Rephrased, any amount of subject material coming through the reservoir is negligible when considered in light of the amount of subject material present in the first diluted material. Additional dilution modules can be included within a device, depending upon the level of dilution ultimately desired. Further, in those applications where one wishes to manipulate a number of different dilutions of a given subject material, e.g., in enzyme assays, binding assays, inhibitor screening assays, and the like, one can aliquot a sample of diluted material from the main channel after each dilution stage, for further manipulation, while the remainder of the material is subject to further dilution stages and manipulations.

Figure 4:
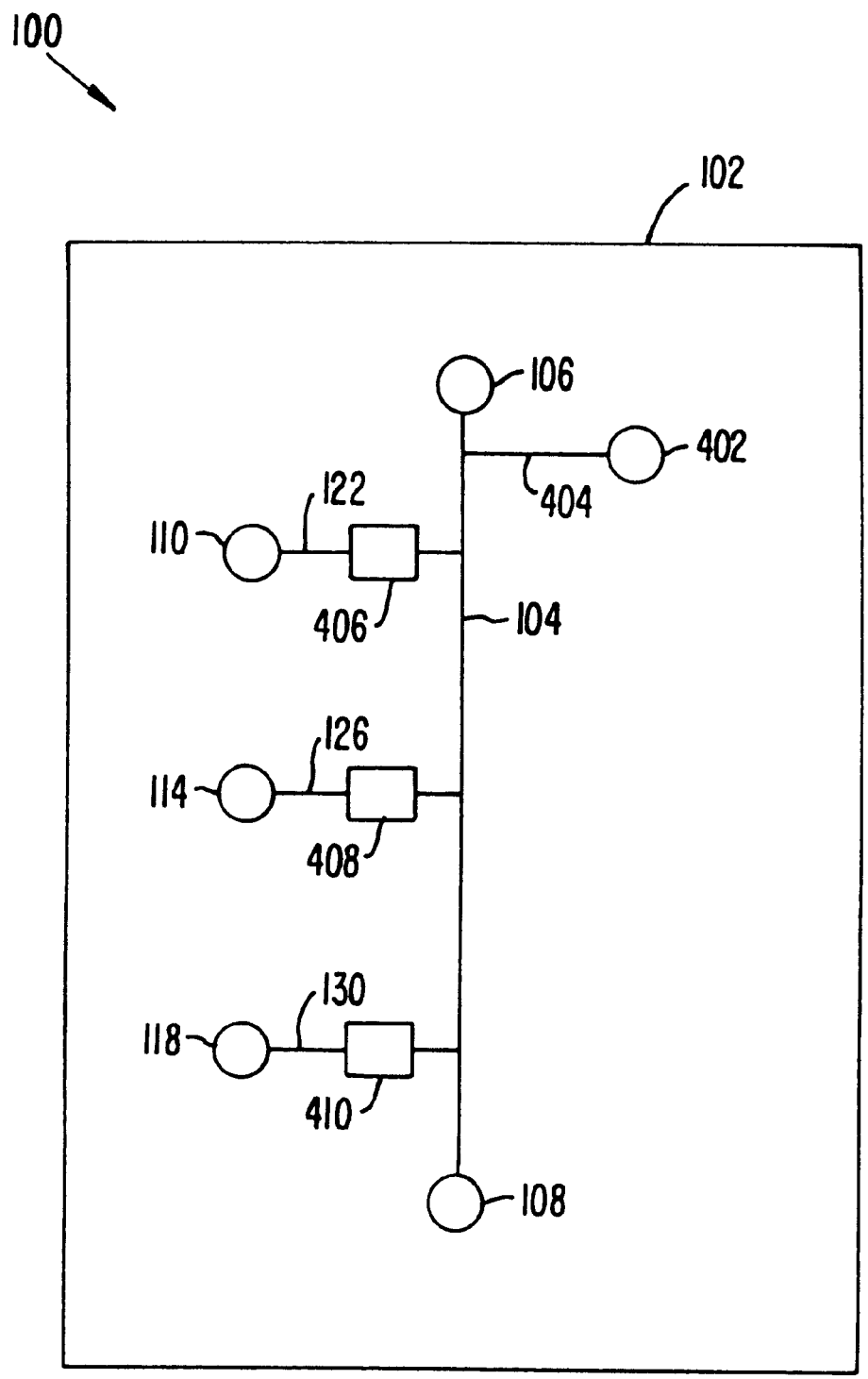
FIG. 4 is a schematic illustration of a further embodiment of a microfluidic device for performing serial dilutions of a subject material in a stepwise format.

Another closely related example of a microfluidic system for performing in situ dilutions is schematically illustrated in FIG. 4. Again, the methods and devices described in this example perform serial dilutions of the subject material, and maintain the volume of material within the main channel by removing a portion of the diluted material from the channel following each step. This example differs from that described above, however, in that it includes a single diluent reservoir 402, but employs mixing chambers or regions, 406, 408 and 410, separate from the main channel 104, for mixing the diluent and subject material, in a number of steps. In particular, a first volume of the subject material is transported from reservoir 106 to reservoir 406, where it is mixed with a first volume of diluent transported to chamber 406 from reservoir 402, to form a first diluted material. Typically, the transport of the subject material and the first volume of diluent is carried out concurrently, although this is not necessary. Typically, the mixing chambers will have a substantially larger cross sectional dimension and/or depth than the channels of the system, to allow the introduction of larger volumes. A second volume of the first diluted material, e.g., typically some fraction of the total volume of the first diluted material, is then transported from mixing chamber 406 to mixing chamber 408, via main channel 104, whereupon it is mixed with a second volume of diluent to create a second diluted material. The second volume of first diluted material and second volume of diluent are selected depending upon the dilution that is desired for this step. Again, the transportation of the first diluted material and the second volume of diluent to mixing chamber 408 is typically carried out concurrently. This step is repeated in mixing chamber 410 and further as needed for the desired ultimate dilution.

III. Concentration

In another aspect, the present invention is directed to methods of performing in situ concentration of samples within microfluidic devices and systems, as well as being directed to the devices and systems themselves. In particular, the devices and systems concentrate a particular subject material electrophoretically, within the channels of the microfluidic device, and are therefore particularly suited for use with electroosmotic fluid direction systems, e.g., as described above. Specifically, in electroosmotic fluid direction, the presence of charged groups within a particular subject material or chemical specie can result in the electrophoretic mobility of that material within the system being different from the electroosmotic mobility of the fluid carrying that material. Depending upon the charge, this may result in the subject material moving through the channels of the system faster or slower than the fluid in which it is disposed. This shifting or electrophoretic biasing of the subject material within its fluid carrier can result in problems where one's goal is to transport the subject material from a first location in the microfluidic system to a second location in the system, substantially unchanged. In particular, these electroosmotic fluid direction systems function by applying a voltage gradient or electric field across the length of a channel along which fluid flow is desired. This same voltage gradient or electric field also causes the charged species within the fluid contained in the channel to electrophorese. Where the voltage gradient is greater, e.g., in lower conductivity fluids, the electrophoresis of the charged species is also greater, while lower voltage gradients, e.g., in high conductivity fluids, result in lower levels of electrophoresis.

The present invention employs both low and high conductivity fluids in the same channel, to affect the concentration of the subject material. Specifically, the subject material is generally provided in a fluid or buffer having a low relative conductivity, and dispensed as a discrete volume or fluid region, into a microscale channel, surrounded by fluid regions (also termed "spacer regions") of high relative conductivity. The fluid of high relative conductivity will typically have a conductivity that is at least two times the conductivity of the low relative conductivity fluid, and preferably, at least five times the conductivity of the low relative conductivity fluid, more preferably at least ten times the conductivity of the low relative conductivity fluid, and often at least twenty times the conductivity of the low relative conductivity fluid. Typically, the low conductivity fluid will have a conductivity in the range of from about 0.1 mS to about 10 mS. The high conductivity fluid typically has a conductivity in the range of from about 0.2 mS to about 100 mS.

When a voltage gradient is applied across the length of the channel, it will result in the movement of the subject material fluid along the channel by electroosmotic flow. The voltage gradient will also result in the electrophoresis of the charged subject material in the same or opposite direction of electroosmotic flow within the channel. The direction of electrophoretic mobility is determined by the charge on the subject material, e.g., either positive or negative. However, once the charged subject material reaches the interface of the low conductivity subject material region and the high conductivity spacer region, the electrophoresis of the charged material will be substantially reduced, because of the lack of a substantial voltage gradient across the high conductivity regions. This results in a "stacking" or concentration of the charged species at or near the interface of the two fluids. A portion of the fluid at or near this interface is then aliquoted from the remainder of the fluid in the channel at a substantially concentrated level, for further processing or analysis, e.g., separation.

An example of a concentrator device, or concentrator elements of a device, for performing this type of concentration is schematically illustrated in FIG. 5. As shown in FIG. 5A, the concentrator includes a main channel 502, a sample introduction channel 504 in fluid communication with the main channel at a first intersection 506, a waste channel 508 in fluid communication with the main channel at a second intersection 510, and an aliquoting channel 512 in fluid communication with the main channel at a third intersection 514. The aliquoting channel may be used to shunt off the concentrated portion of the subject material.

Alternatively, the stacked subject material may merely be subject to further manipulation as is. For example, in screening applications, e.g., employing inhibition assays, binding assays or the like, the concentration of the screened compound at the front of the fluid material that is loaded into the main channel will often be sufficient to ascertain screen results. Similarly, the concentration of species at the front edge of the material region may also act as a stacking process, e.g., like a stacking gel layer in SDS-PAGE or agarose sequencing gels, in order to provide greater resolution in separation applications, e.g., capillary electrophoresis.

As shown the third intersection 514 is provided in the main channel somewhat dislocated from the first and second intersections 506 and 510, respectively, to provide adequate opportunity for the electrophoresis of the charged materials. Again, this distance will generally vary depending upon the nature of the material sought to be concentrated, e.g., its net charge, molecular weight, conformation, or other factors affecting the materials electrophoretic mobility within the channel.

Figure 5A:
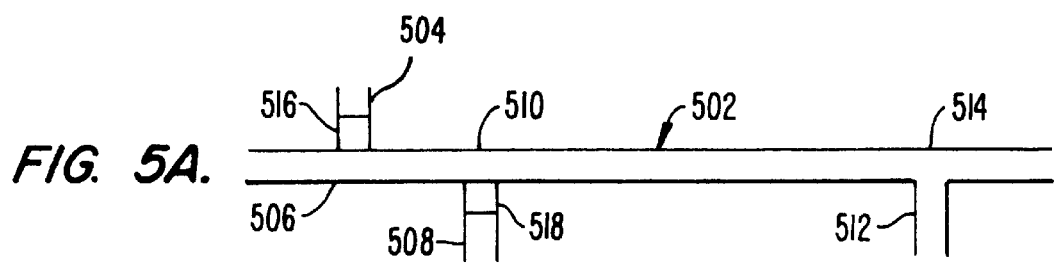
FIGS. 5A through 5E show a schematic illustration of a concentrator element for incorporation into a microfluidic system.

The concentrator illustrated in FIG. 5A also includes shallow regions 516 and 518 within the sample loading and waste channels 504 and 508, respectively, where these channels reach their respective intersections with the main channel 502. These shallow regions generally prevent unwanted flow due to pressure effects associated with the electroosmotic pumping of different fluid regions within a microscale channel intersected by other channels, where those different fluid regions have different conductivities. This is described in substantial detail in U.S. patent application Ser. No. 08/760,446, filed Dec. 6, 1996, now U.S. Pat. No. 5,880,071 and incorporated herein by reference in its entirety for all purposes.

Briefly, in the electroosmotic flow systems described herein, the presence of differentially mobile fluids (e.g., fluids having different conductivities and thus having different electroosmotic or electrokinetic mobilities in the particular system) in a channel may result in multiple different pressures being present along the length of a channel in the system. For example, these electrokinetic flow systems typically employ a series of regions of low and high conductivity fluids (e.g., high ionic concentration spacer regions and low ionic concentration material regions) in a given channel to produce electroosmotic flow. As the low ionic concentration regions within the channel tend to drop the most applied voltage across their length, they will tend to push the fluids through a channel. Conversely, high conductivity fluid regions within the channel provide relatively little voltage drop across their lengths, and tend to slow down fluid flow due to viscous drag.

As a result of these pushing and dragging effects, pressure variations can generally be produced along the length of a fluid filled channel. The highest pressure is typically found at the front or leading edge of the low ionic concentration regions (e.g., the material regions), while the lowest pressure is typically found at the trailing or back edge of these low ionic concentration fluid regions.

By reducing the depth of the channels intersecting the main channel, e.g., the sample introduction and waste channels 516 and 518, relative to the main channel 502, the fluctuations in fluid flow can be substantially eliminated. In particular, in electroosmotic fluid propulsion or direction, for a given voltage gradient, the rate of flow (volume/time) generally varies with the depth of the channel for channels having an aspect ratio of >10 (width:depth). With some minor, inconsequential error for the calculation, this general ratio also holds true for lower aspect ratios, e.g., aspect ratios >5. Conversely, the pressure induced flow for the same channel will vary as the third power of the channel depth. Thus, the pressure build-up in a channel due to the simultaneous presence of fluid regions of differing ionic strength will vary as the square of the channel depth.

Accordingly, by decreasing the depth of the intersecting second channel relative to the depth of the first or main channel by a factor of X, one can significantly reduce the pressure induced flow, e.g., by a factor of $X^3$, while only slightly reducing the electroosmotically induced flow into that channel, e.g., by a factor of X. For example, where the second channel is reduced in depth relative to the first channel by one order of magnitude, the pressure induced flow into that second channel will be reduced 1000 times while the electroosmotically induced flow will be reduced by only a factor of ten. Accordingly, in some aspects, the present invention provides microfluidic devices as generally described herein, e.g., having at least first and second intersecting channels disposed therein, but where the first channel is deeper than the second channel. Generally, the depths of the channels may be varied to obtain optimal flow conditions for a desired application. As such, depending upon the application, the first channel may be greater than about two times as deep as the second channel, preferably greater than about 5 times as deep as the second channel, and often greater than about ten times as deep as the second channel.

Figure 5B:
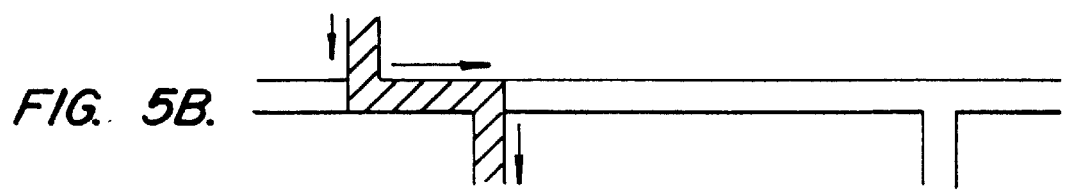
Figure 5C:
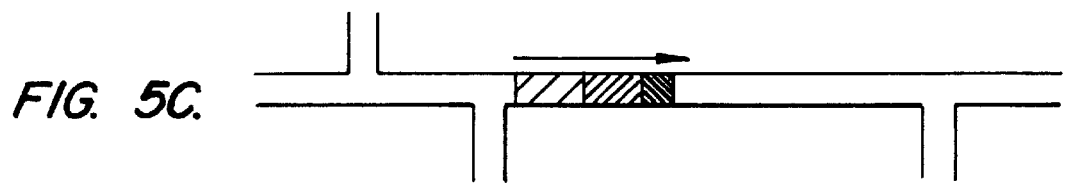
Figure 5D:
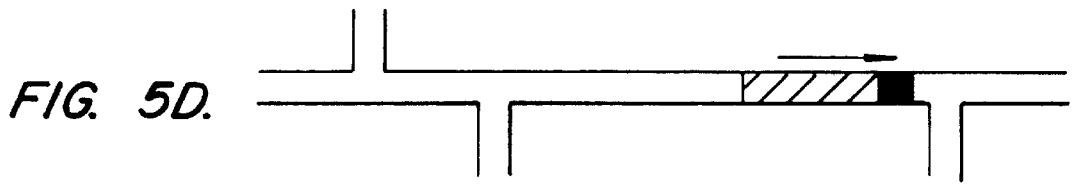

The operation of the concentrator element is schematically illustrated in FIG. 5B through 5E. As shown, the sample fluid containing the subject material and having a low conductivity (shown in grey) is loaded into the main channel by transporting the material from a sample channel 504 to waste channel 508 via the main channel 502, typically by applying a voltage gradient along this path. The direction of fluid flow is indicated by the arrows. As noted above, the sample fluid in the main channel (shaded region) has a low relative conductivity, and is typically bounded by fluid regions having relatively high conductivity (shown unshaded). Transport of the sample fluid into the main channel is typically carried out by application of a voltage gradient between reservoirs that are separately in fluid communication with the sample and waste channels. Switching the voltage gradient across the length of main channel 502, i.e., by applying different voltages at the termini of the main channel, then allows the transport of the subject material along that channel (FIG. 5C). Concurrent with this transport is the electrophoretic stacking of the charged subject material within the subject material fluid, indicated by the darker shading at the front of the sample fluid plug being transported along the main channel (FIGS. 5C and 5D). Although illustrated in terms of the subject material being concentrated at the front of the subject material region, it will be readily appreciated that the charge on the subject material will affect the mobility of that material under an electric field. For example, if the subject material possesses a net charge opposite to that for which concentration is illustrated in FIG. 5B–5D, then the subject material will be concentrated at the back end of the subject material region, relative to the direction of electroosmotic flow.

Figure 5E:
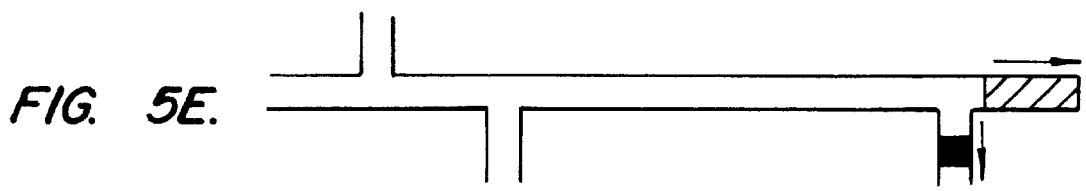

Finally, as shown in FIG. 5E, when the concentrated or stacked portion of the sample fluid reaches the third intersection, the concentrated portion can be shunted off from the remainder of the sample fluid plug by appropriate application of a voltage gradient along that path, effectively resulting in the concentration the subject material. In some cases, it is not necessary to shunt off the concentrated material in order to see the benefit of the concentration of the material. For example, where screening compounds of relatively low concentration, the increased localized concentration of the compound at the front end of the low ionic concentration region resulting from the concentration methods described herein may be sufficient to produce an adequately detectable result.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

We claim:

1. A microfluidic system for diluting a material in a microfluidic device, the system comprising:

a microfluidic device having at least a first main channel disposed therein, said main channel having at least one microscale cross-sectional dimension;

at least a first source of said material in fluid communication with said main channel at a first point along a length of said main channel;

at least a first diluent source in fluid communication with said main channel at a second point along said length of said main channel;

at least a first reservoir in fluid communication with said main channel at a third point along said length of said main channel; and a fluid direction system for delivering diluent and material to said main channel, and combining said diluent with said material to form first diluted material, and for transporting a portion of said first diluted material along said main channel.

2. The microfluidic system of claim 1, wherein, during operation of the device, the fluid direction system directs flow of diluent from the diluent source into the main channel downstream of the first source of the material.

3. The microfluidic system of claim 2, wherein, during operation of the device, the flow rate of the first diluted material downstream of the second point in the main channel and upstream of the third point in the main channel, in a first dilution region, is greater than the flow of the material upstream of the second point.

4. The microfluidic system of claim 3, wherein during operation of the device, the flow rate in the first dilution region, is about 10x that of the flow of the material upstream of the second point.

5. The microfluidic system of claim 3, wherein the first reservoir is fluidly coupled to the main channel through a second channel, wherein the third point comprises a first intersection of the second channel and the main channel, and wherein, during operation of the device, the fluid direction system flows a portion of the first diluted material through the first intersection, into the second channel and into the first reservoir while concomitantly flowing a portion of the diluted material through the first intersection into a first downstream channel region of the main channel.

6. The microfluidic device of claim 5, wherein flow of the first diluted material into the second channel reduces the flow of the first diluted material in the first downstream channel region relative to the first dilution region.

7. The microfluidic device of claim 6, wherein the flow of the first diluted material in the first downstream region is about 1/10x the flow of the first diluted material in the first dilution region.

8. The microfluidic device of claim 6, further comprising a third channel which intersects the main channel downstream of the first downstream channel region at a second channel intersection.

9. The microfluidic device of claim 8, further comprising a second source of diluent fluidly coupled to the third channel.

10. The microfluidic device of claim 9, wherein, during operation of the device, the fluid direction system flows diluent from the second diluent source into the second channel intersection while maintaining flow of the first diluted material into the second channel intersection, thereby providing a second diluted material in a second dilution region of the main channel, which second dilution region is downstream from the second channel intersection.

11. The microfluidic device of claim 10, wherein the flow of the second diluted material in the second dilution region is greater than the flow of the first diluted material in the first downstream channel region.

12. The microfluidic device of claim 11, wherein the flow of the second diluted material in the second dilution region is about 10 x that of the flow of the first diluted material in the first downstream channel region.

13. The microfluidic device of claim 11, further comprising a fourth channel which intersects the main channel at a third channel intersection downstream of the second dilution region.

14. The microfluidic device of claim 13, wherein, during operation of the device, the fluid direction system flows a portion of the second diluted material through the third channel intersection and into the third microscale channel while concomitantly flowing a portion of the second diluted material through the third channel intersection and into a second downstream channel region of the main channel, which second downstream region is downstream of the third channel intersection.

15. The microscale device of claim 14, wherein flow of the second diluted material in the second downstream region is less than flow of the second diluted material in the second dilution region.

16. The microscale device of claim 15, wherein the flow of the second diluted material in the second dilution region is about 10x the flow of the second diluted material in the second downstream region.

17. The microscale device of claim 1, wherein the fluid direction system induces one or more pressure-based flow of one or more fluid in the device.

18. The microscale device of claim 1, wherein the fluid direction system directs one or more electrokinetic flow of one or more fluid in the device.

19. The microscale device of claim 1, wherein the device comprises one or more polymeric materials.

20. The microscale device of claim 19, wherein the polymeric material comprise one or more of: a plastic, a polymethylmethacrylate (PMMA), a polycarbonate, a polytetrafluoroethylene, a polyvinylchloride (PVC), a polydimethylsiloxane (PDMS), or a polysulfone.

21. The microscale device of claim 1, wherein the device comprises one or more silica-based materials.

22. The microscale device of claim 21, wherein the silica based material comprises one or more of: glass, quartz, silicon, polysilicon or gallium arsenide.

* * * * *